US011464661B2

(12) United States Patent
Garrish (10) Patent No.: US 11,464,661 B2
(45) Date of Patent: Oct. 11, 2022

(54) HINGE FOR A BRACE (71) Applicant: Spring Loaded Technology Incorporated, Halifax (CA)

(72) Inventor: Robert Garrish, Halifax (CA)

(73) Assignee: SPRING LOADED TECHNOLOGY INCORPORATED, Halifax (CA)

( * ) Notice: Subject to any disclaimer, the term of this patent is extended or adjusted under 35 U.S.C. 154(b) by 524 days.

(21) Appl. No.: 16/105,313

(22) Filed: Aug. 20, 2018

(65) Prior Publication Data
US 2019/0060100 A1  Feb. 28, 2019

Related U.S. Application Data (63) Continuation of application No. 14/851,191, filed on Sep. 11, 2015, now Pat. No. 10,070,983.

(51) Int. Cl.
*A61F 5/00* (2006.01)
*A61F 5/01* (2006.01)

(52) U.S. Cl.
CPC .......... *A61F 5/0123* (2013.01); *A61F 5/0102* (2013.01); *A61F 2005/0139* (2013.01); *A61F 2005/0153* (2013.01); *A61F 2005/0155* (2013.01); *A61F 2005/0167* (2013.01); *A61F 2005/0169* (2013.01); *A61F 2005/0179* (2013.01)

(58) Field of Classification Search
CPC .... A61F 5/0125; A61F 5/0102; A61F 5/0127; A61F 5/013; A61F 5/0132
See application file for complete search history.

(56) References Cited

U.S. PATENT DOCUMENTS

| | | | | | |
|---|---|---|---|---|---|
| 2,859,451 | A | * | 11/1958 | Mauch ...................... | A61F 2/68 623/39 |
| 3,799,159 | A | * | 3/1974 | Scott ......................... | A61F 2/68 602/16 |
| 3,976,057 | A | * | 8/1976 | Barclay ................. | A61F 5/0125 601/34 |
| 4,433,679 | A | * | 2/1984 | Mauldin ............... | A61F 5/0125 602/16 |
| 5,014,690 | A | * | 5/1991 | Hepburn ............... | A61F 5/0127 602/16 |

(Continued)

*Primary Examiner* — Kim M Lewis
(74) *Attorney, Agent, or Firm* — Ralph E. Jocke; Walker & Jocke (57) ABSTRACT

A hinge for a brace comprises a tensioning element such as an inelastic cord for applying a restorative force to the hinge. A tensioning mechanism, preferably a hydraulic spring, tensions the cord as the hinge is moved from a rest position to a loaded condition. A tensioning member having a peripheral cam surface applies a tensioning force to the cord as the hinge is moved out of the rest position. The tensioning block and the anchoring block may be operatively geared together along an arc of motion so as to provide a generally symmetrical motion of the tensioning and anchoring portions relative to the gusset. When an external force is applied to move the hinge from the rest position the tension on the cord loads the spring, and when the external force is removed the spring applies a restorative force to move the hinge back to the rest position. Optionally the tensioning member may be configured to be disengaged and reengaged by an external actuator.

18 Claims, 7 Drawing Sheets

(56) References Cited

U.S. PATENT DOCUMENTS

| | | | | |
|---|---|---|---|---|
| 5,103,811 | A * | 4/1992 | Crupi, Jr. | A61F 5/024 |
| | | | | 602/16 |
| 5,472,412 | A * | 12/1995 | Knoth | A61F 5/0123 |
| | | | | 428/111 |
| 10,070,983 | B2 * | 9/2018 | Garrish | A61F 5/0123 |
| 10,744,020 | B2 * | 8/2020 | Garrish | A61F 5/013 |
| 2003/0153853 | A1 * | 8/2003 | Houser | A61F 5/0123 |
| | | | | 602/16 |
| 2013/0110020 | A1 * | 5/2013 | Ingimundarson | A61F 5/0123 |
| | | | | 602/16 |
| 2015/0119777 | A1 * | 4/2015 | Garrish | A61F 5/0123 |
| | | | | 602/16 |
| 2015/0374532 | A1 * | 12/2015 | Fedon | A61F 5/0125 |
| | | | | 602/16 |
| 2016/0361222 | A1 * | 12/2016 | Publicover | A63B 23/0494 |
| 2019/0290465 | A1 * | 9/2019 | Fleming | A61F 5/0123 |

* cited by examiner

HINGE FOR A BRACE

FIELD OF THE INVENTION

This invention relates to braces, and in particular to a hinge for a brace for supporting and/or assisting the extension of a limb.

BACKGROUND OF THE INVENTION

As is well known, a limb brace such as a knee brace can perform a purely prophylactic function, or provide an assistive force that helps the user to extend their limb, or both. Knee braces in particular can also provide physical protection against injury, and may for example be used by athletes involved in high-risk sports where there is a relatively high susceptibility to sustaining a knee injury.

Many individuals suffer from knee problems, often due to a prior knee injury. Some such problems can significantly affect mobility and/or the ability to support the injured person. While corrective measures such as exercise and physiotherapy, or in more serious cases surgery, can assist in correcting or partially alleviating some knee problems, there remains a need in many cases for knee support and extension augmentation.

Particularly where there has been ligament damage, for example a tear or strain in the anterior cruciate ligament (ACL), medial collateral ligament (MCL) or lateral collateral ligament (LCL), a knee brace can be used to both provide support and enhance extension strength, and thus reduce the load on the injured knee. Conventional knee braces that provide active assistance to knee extension are designed to yield when the knee is flexed, loading a torsion spring or compression spring in the process. The spring is loaded when the user bends their leg, and when extending their leg the spring unloads applying a force that augments the extension action. This also helps to support the user and prevent collapse if the injured knee buckles.

However, conventional springs do not provide sufficient force to significantly enhance knee extension or resist buckling of the knee. Furthermore, conventional tensioning mechanisms for braces do not provide an adjustable force curve allowing for precise adjustments and retention of the force curve profile over prolonged periods of usage.

It would accordingly be advantageous to provide a tensioning mechanism with an adjustable force curve allowing for precise adjustments and retention of the force curve profile over prolonged periods of usage, which provides effective enhancement of the knee extension action in cases where strength enhancement is needed and resistance to buckling of the knee.

BRIEF DESCRIPTION OF THE DRAWINGS

In drawings which illustrate by way of example only a preferred embodiment of the invention.

DETAILED DESCRIPTION OF THE INVENTION

The invention will be described in the context of a knee brace for humans. However, it will be appreciated that the principles of the invention apply equally to braces for other human body appendages and to braces for animals including (without limitation) horses, dogs and cats.

Figure 1:
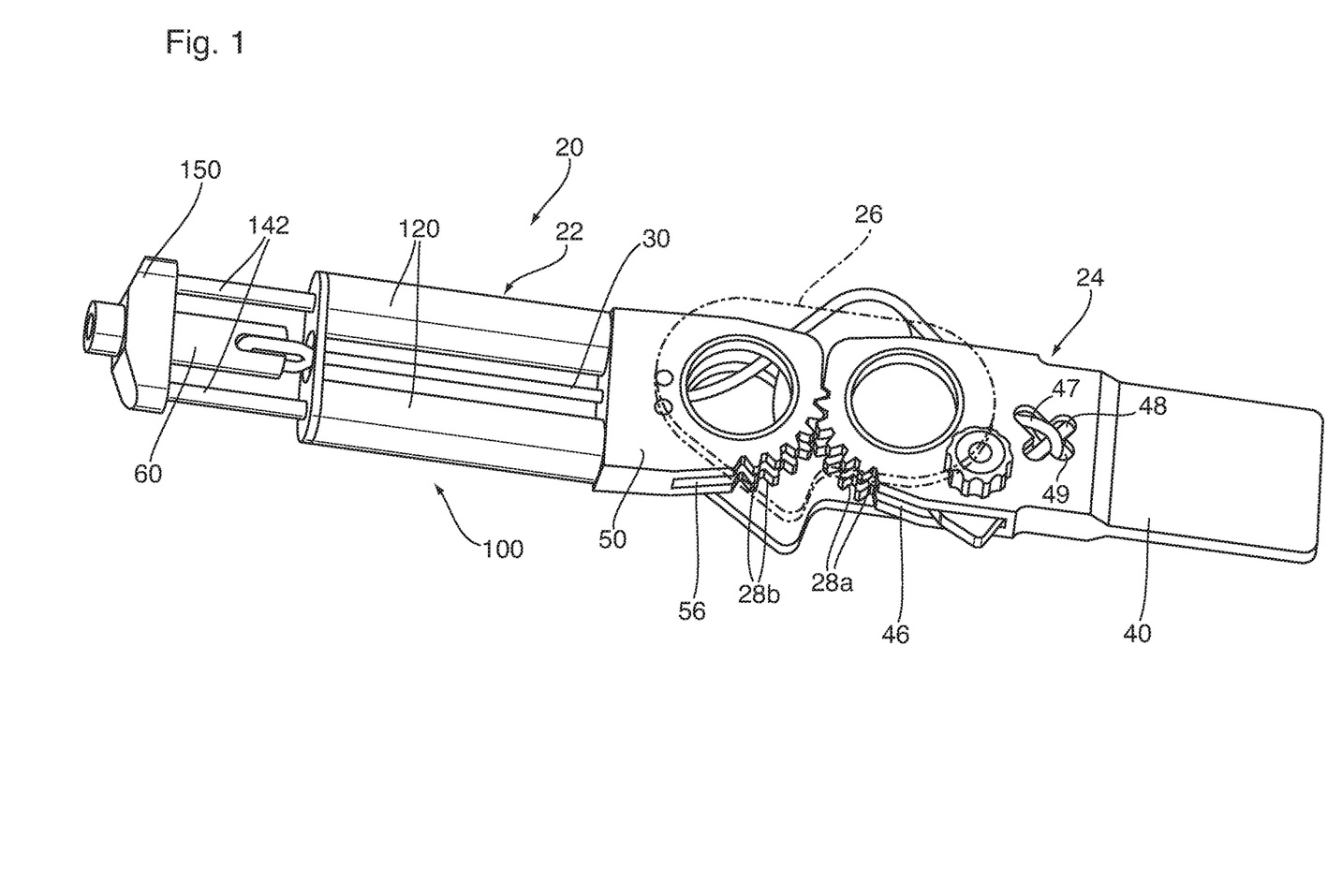
FIG. 1 is a perspective view of an embodiment of a hinge mechanism for a brace according to the invention.
Figure 7:
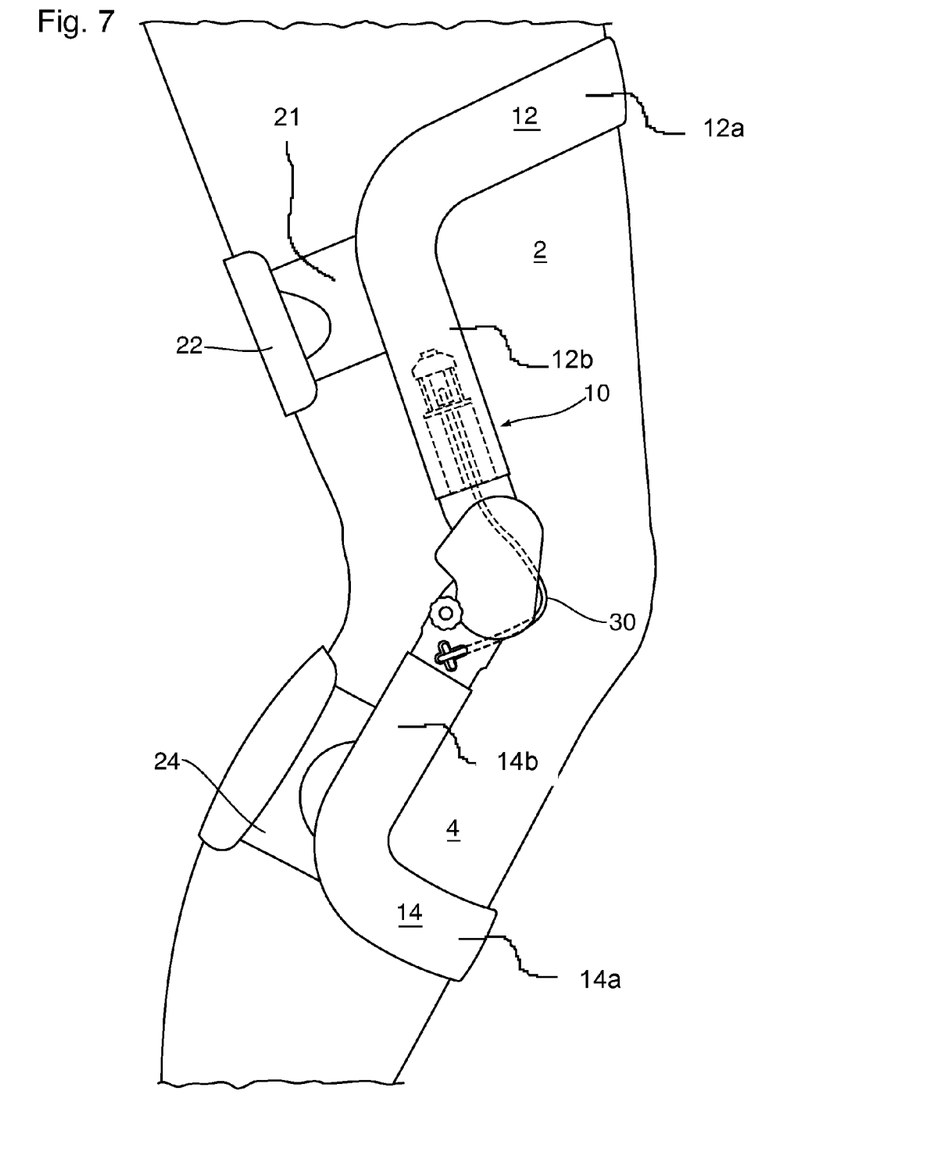
FIG. 7 is a perspective view of the tensioning mechanism of FIG. 1 mounted to a knee brace.

FIG. 1 illustrates an embodiment of the hinge 20 for use in a limb brace, for example the knee brace 10 illustrated in FIG. 7. The knee brace 10 conventionally comprises an upper arm 12 having an engaging portion 12a for engaging against the front or rear of the femoral portion 2 of a user's leg, for example the front of the femoral portion 2, and an attachment portion 12b; and a lower arm 14 having an engaging portion 14a for engaging against the tibial portion 4 of the user's leg, for example the front or rear of the tibial portion 4, and an attachment portion 14b, as is well known. The upper arm 12 is formed with a contour that comfortably engages against the user's leg, which may be padded for additional comfort, and may be secured to the leg by a top strap 21 and an upper cruciate strap 22 as is conventional. The lower arm 12 is formed with a contour that comfortably engages against the user's leg, which similarly may be padded for additional comfort, and may be secured to the leg by a bottom strap 24 and optionally a lower cruciate strap (not shown).

The hinge 20 comprises a tensioning portion 22 and an anchoring portion 24, each pivotally mounted to a gusset 26. In the exemplary embodiment shown anchoring portion 24 is pivotally mounted to the gusset 26 by pin 74 projecting from the recessed portion 45 of the anchoring block 40, and tensioning portion 22 is pivotally mounted to the gusset 26 by pin 58 projecting from the recessed portion 55 of the tensioning block 50. The tensioning portion 22 and an anchoring portion 24 are preferably operatively geared together along an arc of motion, as at cogs 28a, 28b, to ensure a generally symmetrical motion as between the two portions 22, 24 relative to the gusset 26 as the hinge 20 is bent. Embodiments of the hinge in which the tensioning portion 22 and an anchoring portion 24 are not operatively geared together are also possible, however in some cases the particular pathology being treated would benefit from a generally symmetrical motion as between the two portions 22, 24 relative to the gusset 26, and in such cases it can be disadvantageous to allow the free rotation of the tensioning portion 22 and an anchoring portion 24 relative to each other.

In the preferred embodiment the tensioning portion 22 is mounted to the upper arm 12 of the brace. The anchoring portion 24, to which the tensioning element, as illustrated tensioning cord 30 is anchored, is mounted to the lower arm 14 of the brace. This configuration is advantageous because it reduces the strain on the user's leg caused by the weight of the tensioning mechanism, in the embodiment illustrated a hydraulic spring 100, by keeping the spring 100 as close to the hip joint as possible and thus reducing the moment of force on the hip flexors as the knee is raised. However, it will be appreciated that the tensioning portion 22 could be mounted to the lower arm 14 and the anchoring portion 24 mounted to the upper arm 12 without any change in the design of the hinge 20.

Figure 2:
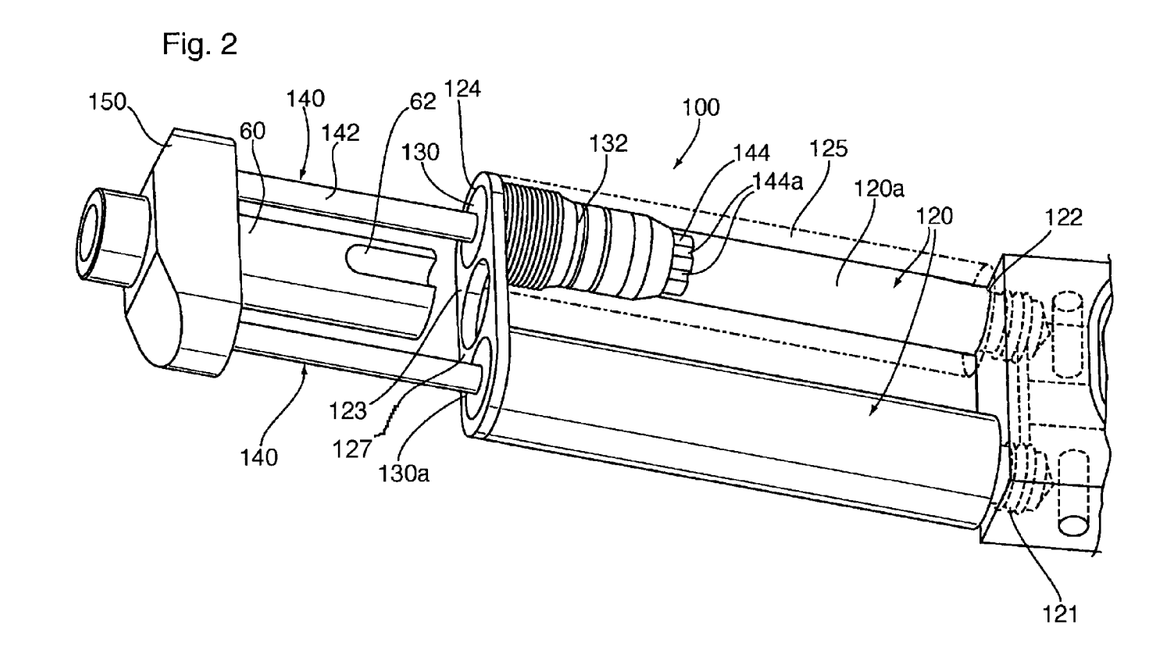
FIG. 2 is a partially broken-away perspective view of the spring in the hinge mechanism of FIG. 1
Figure 3:
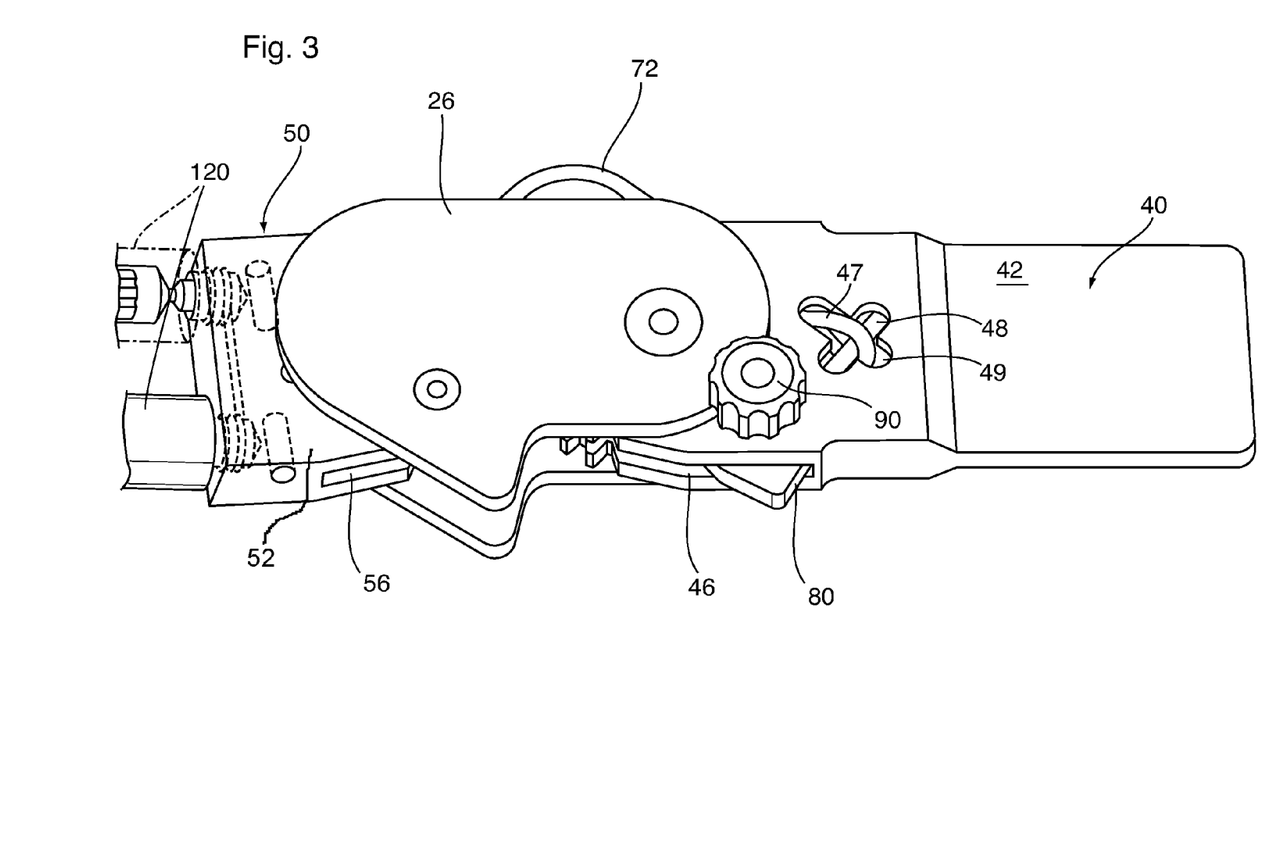
FIG. 3 is a perspective view of the pivoting portion of the hinge mechanism of FIG. 1.

FIG. 2 illustrates the tensioning portion 22, which provides a restorative force for returning the brace 10 to a rest position. In the preferred embodiment the tensioning portion 22 comprises a hydraulic spring 100 comprising a pair of hydraulic cylinders 120 each having a fixed end attached to the tensioning block 50, for example via a threaded nipple 121 engaged to complementary threading in the end of the tensioning block 50. A hydraulic spring of this type is described and illustrated in the applicant's copending U.S. patent application Ser. No. 14/317,447 for a HYDRAULIC TENSION SPRING filed Jun. 27, 2014, which is incorporated by reference herein in its entirety.

In the embodiment illustrated the spring 100 comprises a pair of cylinders 120 each have a closed end 122 and an open end 124. Each cylinder 120 is defined by a liquid-impermeable wall 125 having a thickness that resists deformation under the maximum forces ordinarily encountered in the environment in which the spring 100 is used. The open end 124 of each cylinder 120 is threaded to receive a seal retainer cap 130 with complementary threading, and affixed (for example threadedly engaged to the seal retainer cap 130 as shown) to a bridge 123 that maintains the open ends 124 of the cylinders 120 in fixed spaced relation. The closed ends 122 of the cylinders are threadedly engaged to the tensioning block 50, and the cylinders 120 are thus maintained rigidly and securely in spaced alignment.

Within each cylinder 120 a piston 140 comprises a piston rod 142 slidably disposed through a seal retainer cap 130, for example composed of hardened steel or another suitably durable material capable of being formed to high-precision tolerances, disposed through the open end 124 of each cylinder 120. The seal retainer cap 130 may for example have a threaded exterior engaged to interior threading about the end of the cylinder 120. The piston rod 142 slidably extends from the piston rod cap 150 into the cylinder 120 through a central axial opening 130a through the seal retainer cap 130 and through hydraulic seal 132.

The hydraulic seal 132 defines a liquid containment space 120a within the cylinder 120 that is filled with a liquid, for example a silicone-based liquid or other suitable hydraulic fluid having the desired compressibility characteristics. Thus, when the piston 140 is in the rest position shown in FIG. 2, the liquid fills the liquid containment space 120a, and is in a substantially uncompressed condition.

In the embodiment illustrated the end of the piston rod 142 within the cylinder 120 is provided with a piston guide 144 which is liquid-permeable, for example being provided with axial flow channels 144a through which the hydraulic fluid flows as the piston 140 is depressed into the cylinder 120, and thus moves freely through the liquid containment space 120a while retaining the piston rod 142 in precise axial alignment within the block. The opposite end of each piston rod 142 bears against (or is fixed to) the piston rod cap 150, for example by lodging the ends of each piston rod 142 in a recess (not shown) in the surface of the piston rod cap 150 facing the cylinders 120, to maintain the piston rods 142 in position symmetrically about the centre of the piston rod cap 150 so that substantially equal force is applied to each piston rod 142. The piston rod cap 150 is constrained to axial movement relative to the cylinders 120 by adjusting screw 60, to which the first end of the tensioning cord 30 is fixed, which intrudes into a guide hole 127 formed in the bridge 123 in direct alignment with the adjusting screw 60 as the piston 140 is depressed into the cylinder 120.

Figure 6:
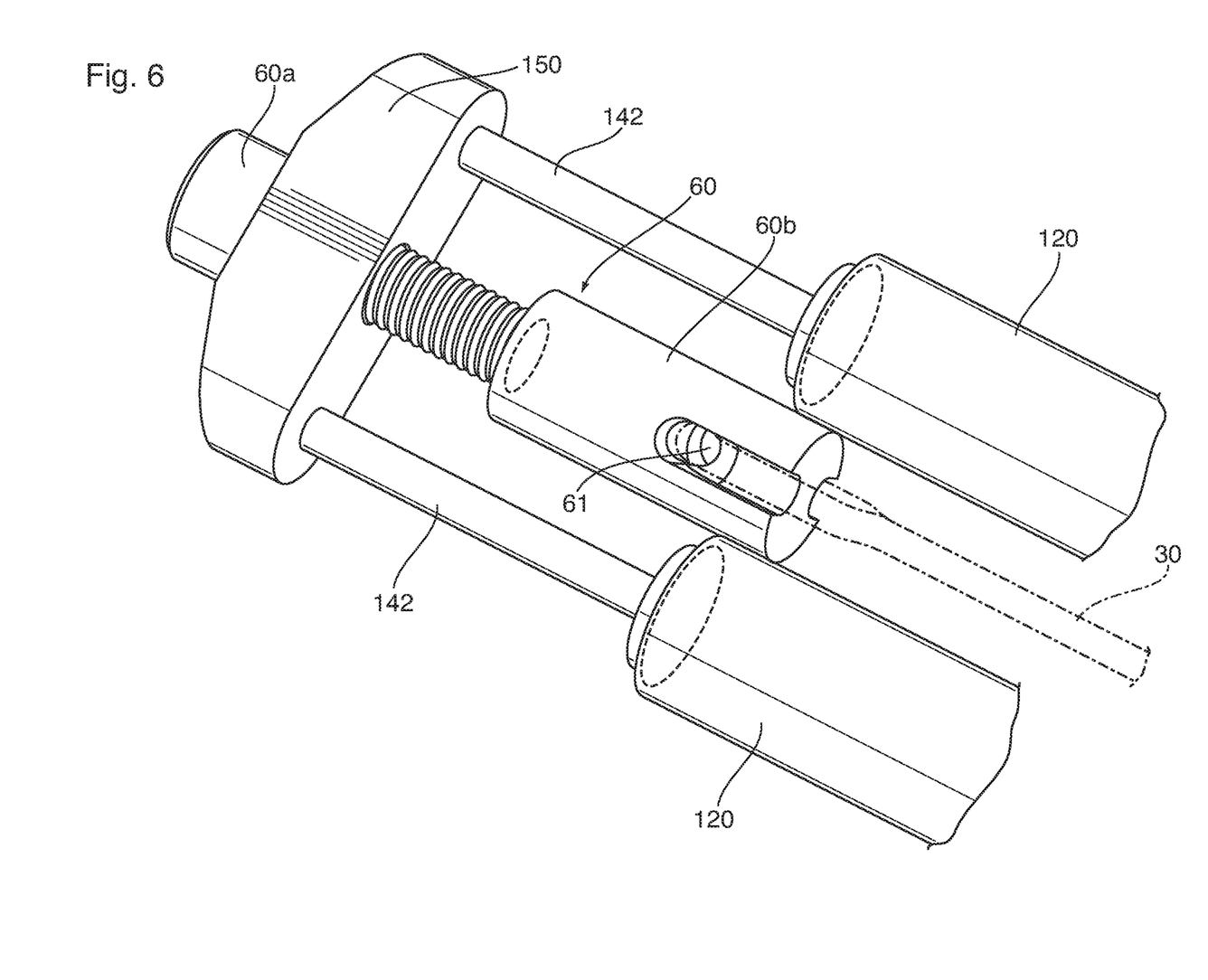
FIG. 6 is an enlarged perspective view of an adjusting mechanism in the tensioning portion of the hinge mechanism.

The adjusting screw 60 is preferably threadedly engaged through the piston rod cap 150, so that fine adjustments to the amount of tension applied to the tensioning cord 30 can be made by rotating the adjusting screw 60. This allows for the tensioning cord 30 to be effectively 'pre-tensioned' in the rest position, or slackened to allow for some degree of motion of the hinge 20 without loading the spring 100, as may be desirable in any particular case. The adjusting screw 60 may comprise two parts, a cap screw 60a and a generally cylindrical anchor portion 60 threaded to receive the screw 60a, as shown in FIG. 6. The end of the anchor portion 60b is optionally provided with a groove on each side as shown, machined into the anchor portion 60b so the cord 30 doesn't bear against a sharp corner. The anchor portion 60b is provided with a lateral opening 61 for receiving the end of the cord 30. The anchor portion 60b thus functions essentially as an eye anchor nut, with a threaded end for receiving the screw 60a and an eye on the other end for attaching the cord 30. Rotation of the cap screw 60a in one direction or the other causes the anchor portion 60b to advance into or recede out of a recess (not shown) in the cap 150, respectively tightening or loosening the tension on the cord 30. The anchor portion 60b, although shown as cylindrical, may be any shape and size capable of receiving the cap screw 60a and the end of the cord 30 with sufficient strength to apply the desired tension.

The anchoring block 40 and the tensioning block 50 may be formed from a rigid, durable material such as metal, for example 7075 aluminum or 17-4 Ph stainless steel or from any other suitable material capable of withstanding the force of the loaded spring 100. Because of the very large forces involved and the small size of the hinge 20, especially the cogs 28a, 28b in the geared region between the two blocks 40, 50, and preferably relatively light to reduce the weight experienced by the user. Each block 40, 50 is preferably formed as an integral piece having two longitudinal portions 42, 44 and 52, 54, respectively. The interlocking cogged ends of the blocks 40, 50 are provided with a recessed portion 45 and 55, respectively (each recessed portion may be alternatively referred to herein as a recessed surface), each forming a respective slot 46, 56 (best seen in FIG. 1) containing a tensioning member, in the embodiment illustrated cam 70, about which the tensioning cord 30 runs to provide the spring loading force as the hinge is bent in the manner described below. The blocks 40, 50 may be optionally provided with transverse openings or cut-out sections as desired (not shown) that do not detract from the structural integrity of the blocks 40, 50, to reduce the overall weight of the hinge 20.

The tensioning cord 30 may be formed from a substantially inelastic cord, for example composed of a polyethylene fibre such as Honeywell Spectra(™) high-strength lightweight polyethylene fibre, which has a very high tensile strength. This type of material also has a very low coefficient of friction, so it easily slides along the cam 70 without significant wear or resistance to the user's motion. The first end of the tensioning cord 30 is affixed to the adjusting screw 60, spliced around the anchoring portion 60b with the portions of the spliced end seated in the grooves 62, and the second end of the tensioning cord 30 is provided with a spliced end 47 disposed around a pin 48 which is in turn trapped in anchoring hole 49. A cord channel 32 provides an egress for the cord 30 from the anchoring block 40, preferably disposed at an angle that provides a smooth transition toward the cam 70.

Figure 4:
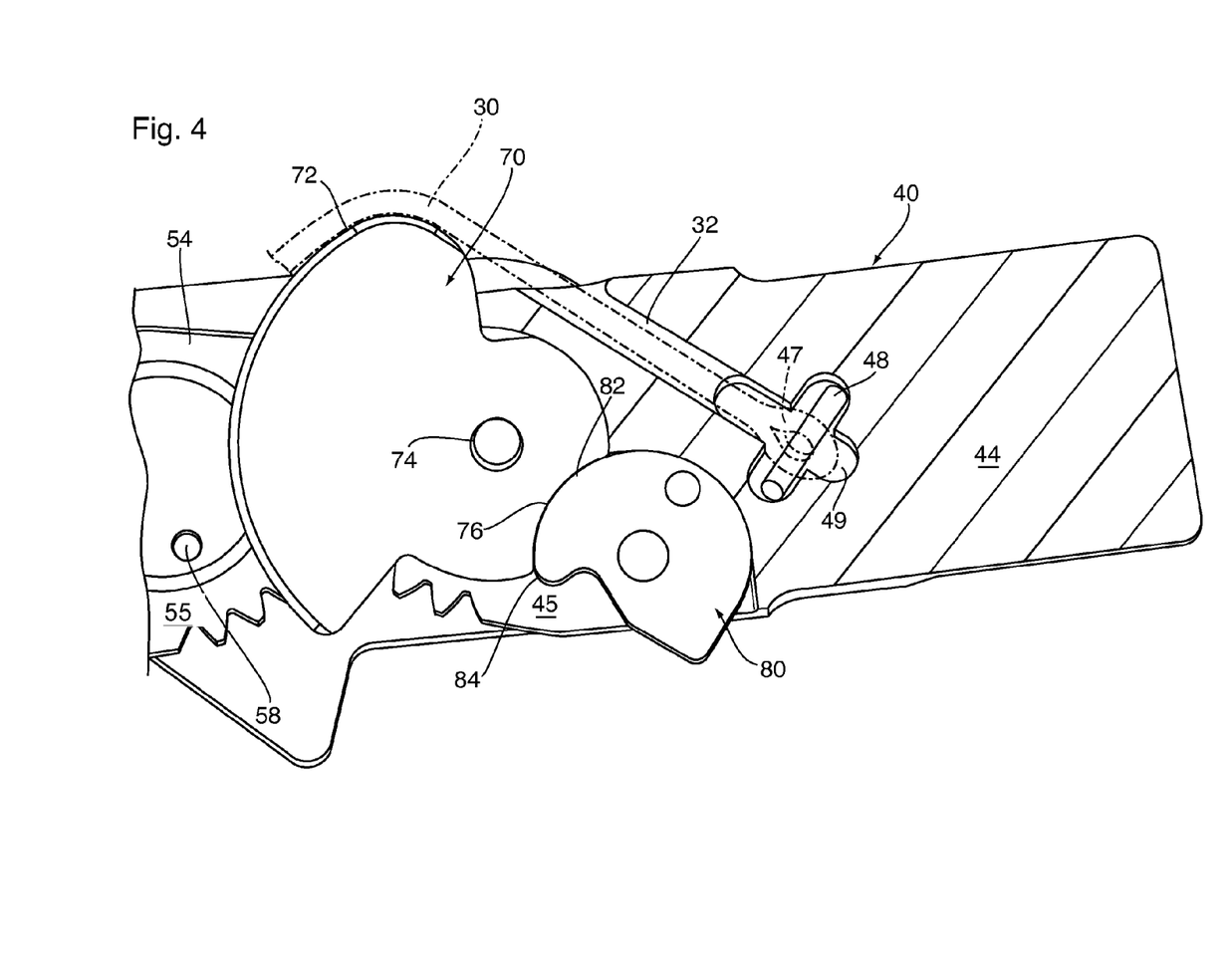
FIG. 4 is a cross-section of the pivoting portion of the hinge mechanism, showing the tensioning lock in the engaged position.
Figure 5:
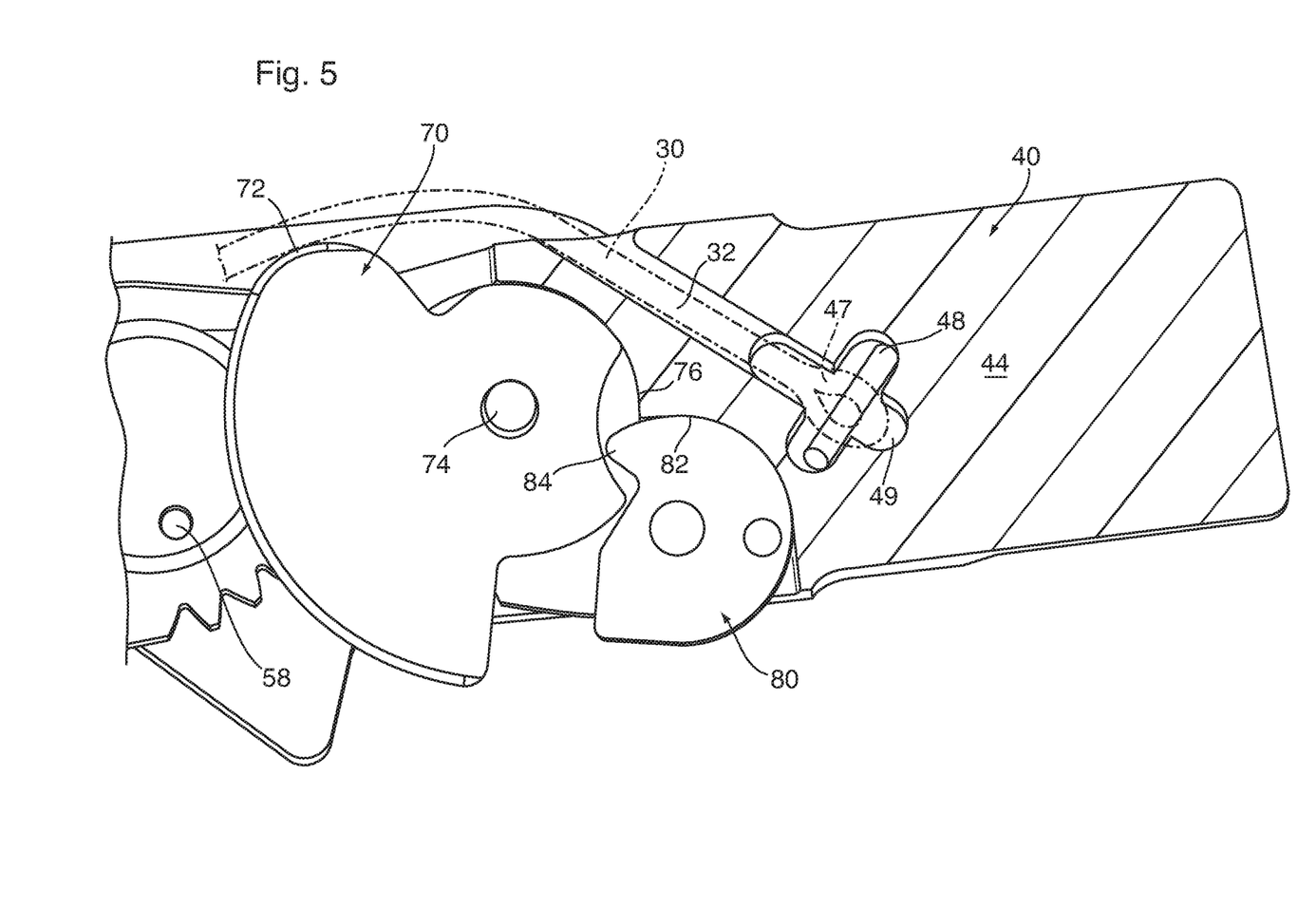
FIG. 5 is a cross-section of the pivoting portion shown in FIG. 4 showing the tensioning lock in the disengaged position.

The tensioning member, cam 70 as illustrated, is best seen in in FIGS. 4 and 5. In the embodiment shown cam 70 is affixed to the recessed surface 45 of the anchoring block 40, for example mounted to the pin 74, preferably pivotally for reasons described below. Cam 70 comprises a peripheral cam edge 72 along which the cord 30 runs, which edge may be transversely concave in order to securely retain the cord 30.

The cam edge 72 may be provided with a non-uniform curvature, for example in the embodiment shown the radius of curvature of the cam edge 72 progressively decreases along the path of the tensioning cord 30 as it approaches the anchoring block 40. Thus, as the hinge 20 is bent and the cord 30 wraps further around the cam edge 72, the force of the cam 70 against the cord 30 increases non-linearly. The cam edge 72 may alternatively be formed with a constant radius of curvature, in which case the increase in the force of the cam 70 against the cord 30 as the hinge 20 is bent will be substantially linear. However, because of the progressively decreasing radius of curvature in the configuration illustrated, the force of the cam 70 against the tensioning cord 30 increases at a higher rate per degree of angular displacement between the tensioning and anchoring portions 22, 24 of the hinge 20 as the cord 30 wraps further around the cam edge 72.

In the embodiment illustrated the cam 70 is releasable, and retained in the operative position by a release member 80. The release member 80 provides an engaging surface 82 complementary to an engaging surface 76 of the cam 70, rotationally fixing the cam 70 in the operative position shown in FIG. 4. A release knob 90 external to the anchoring block 40 is rotationally fixed to the release member 80. When the knob 90 is rotated (clockwise in the embodiment shown), the engaging surface 82 of the release member 80 rotates out of engagement from the engaging surface 76 of the cam 70, allowing the cam 70 to rotate within the slots 46, 56 and effectively retracting the cam edge 72 from the path of the cord 30, as shown in FIG. 5. Thus, in the disengaged position shown in FIG. 5 the cord 30 will not come under tension regardless of the extent to which the hinge 20 is bent, because the cam edge 72 has been fully retracted out of the path of the cord 30. In the preferred embodiment the release member 80 is provided with a nose or projection 84 which, when the knob 90 is rotated back to the engaging position (counter-clockwise in the embodiment shown), applies a force against the engaging surface 76 of the cam 70 to return the engaging surface 82 of the release member 80 into engagement with the engaging surface 76 of the cam 70, thus returning the cam 70 to the operative position shown in FIG. 4 and retaining the cam edge 72 in the path of the tensioning cord 30.

In operation in the environment of a knee brace as shown in FIG. 7, the tensioning cord 30 is affixed to the adjusting screw 60, wrapped around the cam edge 72 of cam 70 and anchored to the anchoring hole 49. The hinge 20 is affixed to a brace 10 in the manner shown in FIG. 7, aligning the pivots 58 and 74 with the joints of the user's knee 6. The adjusting screw 60 is rotated to set the tensioning cord 30 to the desired tension.

As the user bends his or her knee, the upper and lower arms 12, 14 of the brace 10 bend relative to one another, in turn bending the hinge 20. The interlocking cogs 28a, 28b restrain the angular positions of the tensioning and anchoring portions 22, 24 to remain substantially symmetrical about a line between the two pivots 58, 74 as the hinge 20 bends. At the same time, as the hinge 20 bends the tensioning cord 30 wraps around the cam edge 72, applying a force against the first and second ends of the cord 30. The second end of the cord 30 is fixed to the anchoring block 40, and therefore the first end of the cord 30 yields to the force applied by the cam 70 and draws the bridge 150 toward the cylinders 120. This depresses the pistons 140 into the cylinders 120, compressing the hydraulic fluid in the liquid containment space 120a and loading the spring 100. The adjusting screw 60 quickly intrudes into the guide hole 127 in bridge 123, helping to stabilize the piston rods 142 and avoid buckling. The spring 100 continues to load at a rate dictated by the configuration of the cam edge 72, building up potential energy. When the user releases the tension on the brace 10, the potential energy applies restorative force to the brace 10 to return the brace, and the user's leg, to the rest position.

The user may be provided with cams 70 having different configurations of cam edges 72, which can be installed into the hinge to change the shape of the force curve applied by the brace over its range of motion for different activities or as part of a therapy program. The user (or a healthcare provider) may switch from one cam 70 to another by removing knob 90 from the anchoring portion 40 to thereby withdraw the pin from the cam 70, removing the cam 70 through the slot 46 to thereby switch the cam 70 for a different cam 70, and reattaching the knob 90 to the anchoring portion to restore the hinge 20 to an operating condition, ensuring that the tensioning cord 30 is properly wrapped around the cam edge 72.

Various embodiments of the present invention having been thus described in detail by way of example, it will be apparent to those skilled in the art that variations and modifications may be made without departing from the invention. The invention includes all such variations and modifications as fall within the scope of the appended claims.

The invention claimed is:
1. A hinge for a limb brace, the hinge comprising:
   a) a tensioning block connectable to a first attachment portion of a brace for engaging a limb on a first side of a joint;
   b) an anchoring block connectable to a second attachment portion of the brace for engaging the limb on a second side of the joint;
   c) a gusset member pivotally connected to the tensioning block at a first pivot point and pivotally connected to the anchoring block at a second pivot point that is spaced from the first pivot point, whereby the tensioning block and the anchoring block are operatively geared together along an arc of motion and are movable relative to each other between a rest position and a flexed position;
   d) a tensioning system comprising:
      i) a flexible tensioning element extending between a first end connected to the tensioning block and a second end connected to the anchoring block; and
      ii) a tensioning member having a peripheral surface about which the tensioning element is disposed and that is configured to apply a tensioning force to the tensioning element when the hinge is moved by an external force from the rest position toward the flexed position;
   the tensioning system being configured to generate a restorative force in response to the tensioning force when the hinge is moved from the rest position toward the flexed position and the tensioning element is con- figured to carry the restorative force between the tensioning block and the anchoring block to urge the hinge back to the rest position.

2. The hinge of claim 1, further comprising an adjusting mechanism that is manipulable by a user to change the tension of the tensioning member when the hinge is in the rest position, thereby changing the tensioning force that is applied when the hinge is moved toward the flexed position.

3. The hinge of claim 2, wherein the adjusting mechanism comprises a rotatable member that is connected to the first end of the tensioning element, whereby rotating the rotatable member in one direction increases the tension in the tensioning element and rotating the rotatable member in an opposing direction decreases the tension in the tensioning element.

4. The hinge of claim 3, wherein the rotatable member is directly or indirectly connected to the tensioning block.

5. The hinge of claim 1, wherein the tensioning member includes a cam comprising the peripheral surface.

6. The hinge of claim 5, wherein the peripheral surface includes a concave region to receive and laterally retain the tensioning element.

7. The hinge of claim 1, wherein the peripheral edge has a non-uniform curvature such that a radius of curvature of the peripheral edge progressively changes along its length as it approaches the anchoring block, whereby the tensioning force applied to the tensioning member increases non-linearly as the hinge moves away from the rest position.

8. The hinge of claim 1, wherein the second end of the tensioning element is fixedly connected to an anchoring point within the anchoring block, and further comprising a channel extending through the anchoring block from the anchoring point to an open end through which a portion of the tensioning element is movably received.

9. The hinge of claim 8, wherein the channel is aligned with a concave region of the peripheral surface that is configured to receive and laterally retain the tensioning element.

10. The hinge of claim 1, wherein the tensioning block and the anchoring block are operatively geared together so as to provide a generally symmetrical motion of the tensioning and anchoring blocks relative to the gusset.

11. The hinge of claim 1, wherein the tensioning block comprises a rigid tensioning block that comprises integrally formed tensioning cogs, and wherein the anchoring block comprises a rigid anchoring block to which the second end of the tensioning element is connected and that comprises integrally formed anchoring cogs that operatively mesh with the tensioning cogs.

12. The hinge of claim 1, wherein the tensioning element comprises a substantially inelastic cord, and wherein the tensioning system comprises a tensioning mechanism for tensioning the tensioning element as the hinge is moved from the rest position to a loaded condition, wherein one end of the tensioning element is connected to the tensioning mechanism and the other end of the tensioning element is fixed to the tensioning block or the anchoring block.

13. The hinge of claim 12, wherein the tensioning mechanism is connected to the tensioning block, the first end of the tensioning element is connected to the tensioning mechanism and the second end of the tensioning element is connected to the anchoring block.

14. The hinge of claim 12, wherein the tensioning mechanism comprises a hydraulic spring that is loaded when the hinge is moved from the rest position toward the flexed position.

15. The hinge of claim 14, wherein the hydraulic spring comprises at least one piston rod slidably disposed in at least one cylinder, an exposed portion of the piston rod having a piston rod cap to which the first end of the tensioning element is secured.

16. The hinge of claim 15, wherein the first end of the tensioning element is secured to an adjusting screw disposed through the rod cap and movable relative to the piston rod cap to increase or decrease a tension on the tensioning element.

17. The hinge of claim 1, wherein the tensioning member is selectably movable by a user between an engaged position in which the peripheral edge is positioned to engage the tensioning element and a retracted position in which the peripheral edge is retracted out of the path of the tensioning element thereby disengaging the tensioning system so that the hinge is not urged back toward the rest position.

18. A limb brace comprising:
   a) a first attachment portion configured to engage a limb on a first side of a joint;
   b) a second attachment portion movably connected to the first attachment portion and configured to engage the limb on a second side of the joint;
   c) a hinge comprising
      i) a tensioning block connected to the first attachment portion;
      ii) an anchoring block connected to the second attachment portion; and
      iii) a gusset member pivotally connected to the tensioning block at a first pivot point and pivotally connected to the anchoring block at a second pivot point that is spaced from the first pivot point, whereby the tensioning block and the anchoring block are operatively geared together along an arc of motion and are movable relative to each other between a rest position and a flexed position;
   d) a tensioning system comprising:
      i) a flexible tensioning element extending between a first end connected to the tensioning block and a second end connected to the anchoring block; and
      ii) a tensioning member having a peripheral surface about which the tensioning element is disposed and that is configured to apply a tensioning force to the tensioning element when the hinge is moved by an external force from the rest position toward the flexed position;
   the tensioning system being configured to generate a restorative force in response to the tensioning force when the hinge is moved from the rest position toward the flexed position and the tensioning element is configured to carry the restorative force between the tensioning block and the anchoring block to urge the hinge back to the rest position.

* * * * *